(12) United States Patent
Carbonell et al.

(10) Patent No.: US 9,207,217 B2
(45) Date of Patent: Dec. 8, 2015

(54) ACCESS HOLE COVER ULTRASONIC INSPECTION TOOLING

(71) Applicant: WESTINGHOUSE ELECTRIC COMPANY LLC, Cranberry Township, PA (US)

(72) Inventors: John R. Carbonell, Ooltewah, TN (US); Roy C. May, Hixson, TN (US); Charles R. Barrett, Ooltewah, TN (US)

(73) Assignee: Westinghouse Electric Company LLC, Cranberry Township, PA (US)

( * ) Notice: Subject to any disclaimer, the term of this patent is extended or adjusted under 35 U.S.C. 154(b) by 514 days.

(21) Appl. No.: 13/832,251

(22) Filed: Mar. 15, 2013

(65) Prior Publication Data

US 2014/0260631 A1    Sep. 18, 2014

(51) Int. Cl.
*G01N 29/265* (2006.01)
*G21C 17/003* (2006.01)
*G01N 29/22* (2006.01)

(52) U.S. Cl.
CPC ............ *G01N 29/221* (2013.01); *G01N 29/227* (2013.01); *G01N 29/265* (2013.01); *G01N 2291/267* (2013.01)

(58) Field of Classification Search
CPC ... G01N 29/11; G01N 29/07; G01N 29/4427; G01N 29/48; G01N 29/043; G01N 29/265; G01N 29/0609; G01N 29/262; G01N 29/225; G21C 17/003; G21C 17/01; G21C 17/013; G21C 17/017; G21C 19/207; G21C 19/00; C21C 17/007
USPC .............. 73/618–627, 865.8, 866.5; 376/260, 376/392, 249
See application file for complete search history.

(56) References Cited

U.S. PATENT DOCUMENTS

| | | | | |
|---|---|---|---|---|
| 5,568,527 | A | * | 10/1996 | Richardson et al. .......... 376/245 |
| 5,586,155 | A | * | 12/1996 | Erbes et al. ................... 376/249 |
| 6,459,748 | B1 | | 10/2002 | Everett et al. |
| 2006/0222138 | A1 | * | 10/2006 | Shimamura et al. .......... 376/260 |
| 2006/0226668 | A1 | * | 10/2006 | Smith et al. .................. 294/86.1 |
| 2006/0227921 | A1 | * | 10/2006 | Smith et al. ................... 376/260 |

(Continued)

FOREIGN PATENT DOCUMENTS

JP    2006313152 A    11/2006

OTHER PUBLICATIONS

International Search Report and Written Opinion of the International Searching Authority for PCT/US2014/013810 dated May 16, 2014.

*Primary Examiner* — Helen Kwok
(74) *Attorney, Agent, or Firm* — Richard J. Coldren; Westinghouse Electric Company LLC

(57) ABSTRACT

This invention relates generally to ultrasonic inspection of welds and more particularly, to apparatus and methods for ultrasonic inspection of welds on access hole covers found in boiling water reactors having jet pumps. The apparatus includes a base, a center frame coupled to the base and projecting vertically relative to the access hole cover, a radial arm structured to rotate on the center frame and having attached thereto a first pneumatic linear thruster and a second pneumatic linear thruster, and a skew motor assembly and transducer are attached to the first pneumatic linear thruster for scanning the access hole cover weld. The skew motor assembly is structured to control the angle of the transducer and the first pneumatic linear thruster is structured to raise and lower the transducer.

12 Claims, 6 Drawing Sheets

(56) References Cited

U.S. PATENT DOCUMENTS

| | | | |
|---|---|---|---|
| 2007/0189858 A1* | 8/2007 | Nakagawa et al. | 405/190 |
| 2007/0253518 A1* | 11/2007 | Shimamura et al. | 376/260 |
| 2009/0314089 A1 | 12/2009 | Brignac et al. | |
| 2010/0150296 A1* | 6/2010 | Togasawa et al. | 376/260 |
| 2012/0243649 A1* | 9/2012 | Shimamura et al. | 376/249 |

* cited by examiner

ACCESS HOLE COVER ULTRASONIC INSPECTION TOOLING

BACKGROUND

1. Field

This invention relates generally to ultrasonic inspection of welds and more particularly, to apparatus and methods utilized for the ultrasonic inspection of welds on access hole covers found in boiling water reactors containing jet pumps.

2. Description of Related Art

In general, a BWR produces electrical power by heating water to its boiling temperature in a reactor vessel that contains a nuclear fuel core in order to generate steam which is used in turn to drive a steam turbine. The nuclear fuel core consists of a plurality of fuel bundle assemblies. As shown in FIG. 1, in a BWR, feedwater enters a reactor vessel 110 via a feedwater inlet 112. The feedwater flows downwardly through a downcomer annulus 116 to a core lower plenum 124. The downcomer annulus 116 is an annular region located between the reactor vessel and a core shroud 118. The feedwater then enters a nuclear fuel core 120 which includes a plurality of fuel assemblies 122. The core shroud 118 is a stainless steel cylinder which surrounds the nuclear fuel core 120. A mixture of water and steam enters a core upper plenum 126 under the shroud head 128. Jet pump assemblies 142 are circumferentially distributed around the core shroud 118. This core shroud 118 is supported by a shroud support 51 and a shroud support plate 152 is welded to the shroud support 151.

During the construction of some BWRs, access holes were cut into the core shroud support plate to provide personnel a means of passage into the core lower plenum. Upon completion of construction, these holes were covered by welding a plate in order to ensure a leak-tight barrier between the annulus and the lower plenum. Inspection of these welds is conducted on a routine basis to assure that they remain leak tight and to identify any potential concerns for defects. The inspection is typically carried out using conventional ultrasonic inspection techniques known in the art.

Non-destructive evaluation (NDE) methods, such as ultrasonic testing (UT), are known in the art and are typically employed to inspect a structure for defects. In general, high frequency sound waves are applied to the structure being tested using one or more transducers. The transducers typically comprise piezocrystal elements that are excited by an electrical voltage in order to induce the ultrasonic waves in the structure. When the sound waves interact with something (e.g., a void; a crack or other defect) having a significant difference in impedance from that of the propagation medium, a portion of the sound is either reflected or diffracted back to the source from which it originated. Detection and quantification of the returned sound pattern is used to determine the characteristics of the reflecting medium. The results obtained from the inspection are utilized to assess the condition and integrity of the structure. Assessment of the structure is based on the characteristics of the detected defects, such as, for example, the size, orientation and location of the defects. The more precise and accurate the inspection technique and data obtained, the more reliable is the assessment for determining the condition of the structure.

It is an object of the invention to provide apparatus and methods for the ultrasonic inspection of the welds on access hole covers found in boiling water reactors, e.g., the shroud support plate, having jet pumps to detect defects in the welds in order to assure that defects are identified and resolved such that a serious situation can be prevented.

SUMMARY

These and other objects are achieved by the embodiments described herein which provide an apparatus for ultrasonic inspection of an access hole cover weld in a boiling water reactor containing jet pumps. The apparatus includes a base in contact with an access hole cover, a center frame coupled to the base and projecting vertically relative to the access hole cover, a radial arm having a first end and a second opposite end wherein the said forth radial arm is attached to the center frame and is structured to rotate on the center frame, a first pneumatic linear thruster attached to the first end of the said radial arm, a second pneumatic linear thruster attached to the second opposite end of the said radial arm, the second pneumatic linear thruster having an upper end and a lower end, a skew motor assembly attached to the first pneumatic linear thruster wherein the said forth skew motor has an upper end and a lower end, and a transducer attached to the lower end of the said skew motor assembly for scanning the access hole cover weld. The said skew motor assembly is structured to control angle of the transducer relative to a normal line perpendicular to a tangential line of circumference of the access hole cover weld and the first pneumatic linear thruster is structured to raise and lower the transducer.

In another aspect, the invention provides a method for ultrasonic inspection of an access hole cover weld in a boiling water reactor containing jet pumps. The method includes delivering an ultrasonic inspection apparatus to a shroud support plate and positioning the ultrasonic inspection apparatus substantially in the center of an access hole cover for conducting ultrasonic inspection of the access hole cover weld. The apparatus includes a base in contact with an access hole cover, a center frame coupled to the base and projecting vertically relative to the access hole cover, a radial arm having a first end and a second opposite end wherein the said forth radial arm is attached to the center frame and is structured to rotate on the center frame, a first pneumatic linear thruster attached to the first end of the said radial arm, a second pneumatic linear thruster attached to the second opposite end of the said radial arm, the second pneumatic linear thruster having an upper end and a lower end, a skew motor assembly attached to the first pneumatic linear thruster wherein the said forth skew motor has an upper end and a lower end, and a transducer attached to the lower end of the said skew motor assembly for scanning the access hole cover weld. The said skew motor assembly is structured to control angle of the transducer relative to a normal line perpendicular to a tangential line of circumference of the access hole cover weld and the first pneumatic linear thruster is structured to raise and lower the transducer. The method further includes employing the ultrasonic inspection apparatus for performing ultrasonic testing of the access hole cover weld.

In certain embodiments, positioning of the ultrasonic inspection apparatus includes securing the base of the apparatus to the access hole cover, raising the first and second pneumatic linear thrusters, rotating the apparatus to position the radial arm in a desired direction, extending the radial arm to a desired distance in the desired direction, lowering the first and second pneumatic linear thrusters to contact the access hole cover, unsecuring the base of the apparatus from the access hole cover, raising the said forth base of the apparatus off of the access hole cover, driving the radial arm in a desired direction at a desired distance, raising the first and second pneumatic linear thrusters such that the said base contacts the a access hole cover, a securing the apparatus to the access hole cover, and repeating these steps until the apparatus is positioned in the center of the access hole cover.

BRIEF DESCRIPTION OF THE DRAWINGS

A further understanding of the invention can be gained from the following description of the preferred embodiments when read in conjunction with the accompanying drawings in which.

DESCRIPTION OF THE PREFERRED EMBODIMENTS

The invention relates to apparatus and methods for performing ultrasonic inspection of access hole cover welds in a nuclear reactor containing jet pumps, such as a boiling water reactor.

The apparatus and methods of the invention generally perform ultrasonic examinations to obtain maximum volumetric coverage of the weld area joining the access hole cover to the shroud support plate (SSP) in order to detect and identify any defect(s) in the weld.

The apparatus (e.g., tool or tooling) of the invention includes the following three main scanning axes for ultrasonic inspection: tool axial rotate, radial extend/retract arm, and transducer skew angle adjustment. The tool axial rotate scanning axis controls the rotation of the tool about the tool center vertical axis. The radial extend/retract arm scanning axis controls the position of the arm radially inward and outward from the tooling center. The transducer skew angle adjustment scanning axis controls the angle of the transducer relative to the normal line perpendicular to the tangential line of the access hole cover circumference. Each of these scanning axes is controlled by a motor having position feedback via a resolver. Non-feedback axes of motion are controlled by a pneumatic programmable logic controller (PLC) station.

Figure 1:
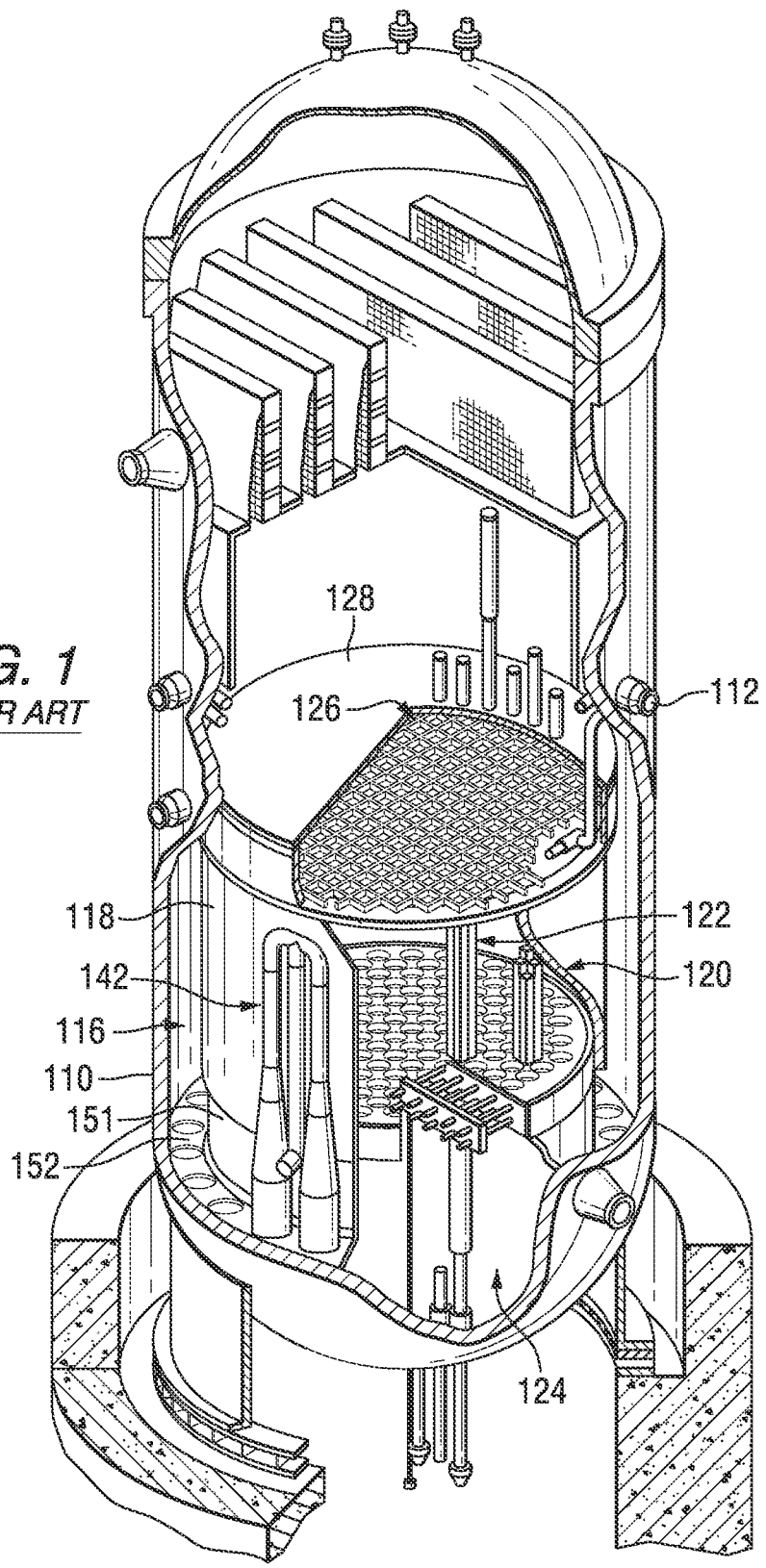
FIG. 1 is a schematic showing a partially cutaway perspective view of a conventional BWR containing jet pumps, in accordance with the prior art.
Figure 2:
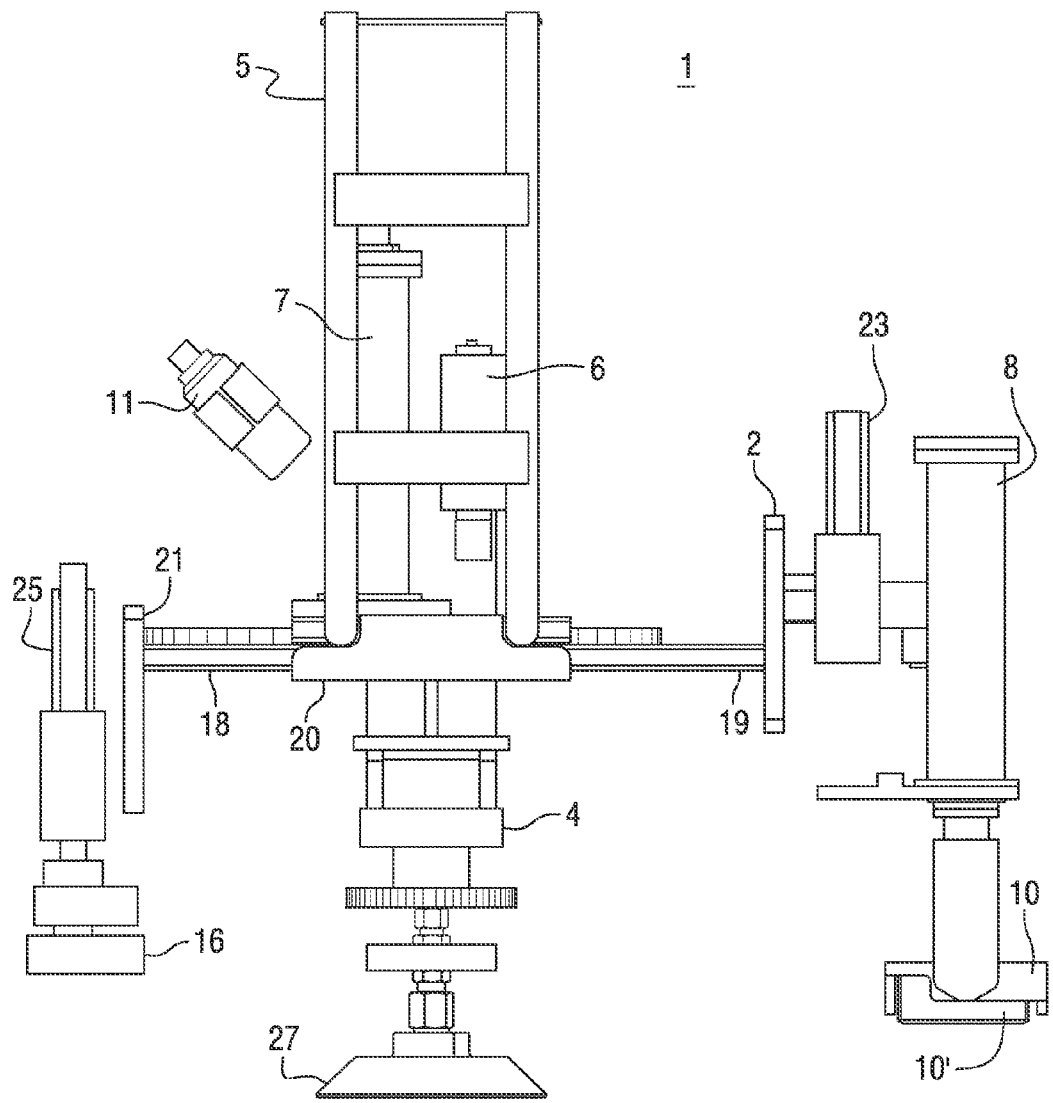
FIG. 2 is a front view of an ultrasonic tool including a vacuum cup to secure the tool in place, in accordance with certain embodiments of the invention.

FIG. 2 shows a front view of an access hole cover ultrasonic inspection tooling 1 in accordance with certain embodiments of the invention. The tooling 1 includes a radial arm assembly 2, a turret 4, and a lifting frame 5. The radial arm assembly 2 includes a radial arm housing 20 and a radial arm 18 having a first end 19 and a second opposite end 21. The radial arm assembly 2 is attached to the turret 4 and is structured to rotate on the turret 4 about the center of the tooling 1. The lifting frame 5 is attached to the radial arm assembly 2 and is structured to be engaged for lifting the tooling 1 during its installation and removal. A first pneumatic linear thruster 23 is attached to the first end 19 of the radial arm 18 and a second pneumatic linear thruster 25 is attached to the second end 21 of the radial arm 18.

A skew motor assembly 8 is attached to the first pneumatic linear thruster 23. A lower end of the skew motor assembly 8 has attached thereto a transducer gimbaling 10 which is coupled to a transducer 10'. The skew motor assembly 8 is structured to control the angle of the transducer 10' relative to a normal line perpendicular to a tangential line of the circumference of the access hole cover (not shown). The first pneumatic linear thruster 23 (which is coupled to the skew motor assembly 8) is structured to raise and lower the transducer 10'. A pneumatic cylinder (not shown) is positioned above the transducer 10' and plumbed with the pneumatic linear thruster 23. When actuated, the pneumatic cylinder will lock in place the transducer 10'.

The first pneumatic linear thruster 23 and the pneumatic cylinder (not shown) are operable to extend the transducer 10' down for contact scanning and to retract the transducer up for immersion scanning. Thus, the tooling 1 is capable of performing two separate scanning techniques, contact and immersion, without the need for significant tooling adjustments or modifications. In certain embodiments, the only change needed to transition between contact and immersion scanning techniques is to replace the transducer 10' due to any limits in its capability relating to one technique or the other.

The tooling 1 also includes an axial rotate motor assembly 6 and a radial extend/retract motor assembly 7. The axial rotate motor assembly 6 is coupled to a rear portion of the lifting frame 5 and the radial arm assembly 2 (near the radial center point) and is structured to control the rotation of the tooling 1 about its center vertical axis. The radial extend/retract motor assembly 7 is coupled to the radial arm assembly 2 (near the radial center point) and is structured to control the position of the arm radially inward and outward from the center of the tooling 1.

A contact pad 16 is connected to a lower end of the second pneumatic linear thruster 25 which is structured to raise and lower the contact pad 16.

The first and second pneumatic thrusters 23,25 are controlled independently such that one can raise or lower without the other one being raised or lowered.

The tooling 1 also includes a vacuum cup 27 (e.g., a base) coupled to turret 4. The vacuum cup 27 is structured to provide secure attachment to a surface of the access hole cover (not shown). Further, a camera assembly 11 is attached to the lifting frame 5 and is structured to take photographs to provide visual feedback.

As previously mentioned, the tooling 1 can perform both contact and immersion ultrasonic testing techniques. These techniques are typically performed by either raising (retracting upward) or lowering (extending downward) the first pneumatic linear thruster 23 which has the transducer 10' attached thereto. The pneumatic cylinder (not shown in FIG. 2) locks into place the transducer 10' for immersion scanning. The distance raised from the access hole cover surface will be a pre-determined water path position. If the first pneumatic linear thruster 23 is raised, the pneumatic cylinder extends to apply a contact plate to a top surface of the transducer 10' to prevent it from moving. If the first pneumatic linear thruster 23 is lowered, the pneumatic cylinder retracts to allow the transducer 10' to gimbal freely for contact scanning.

Figure 3:
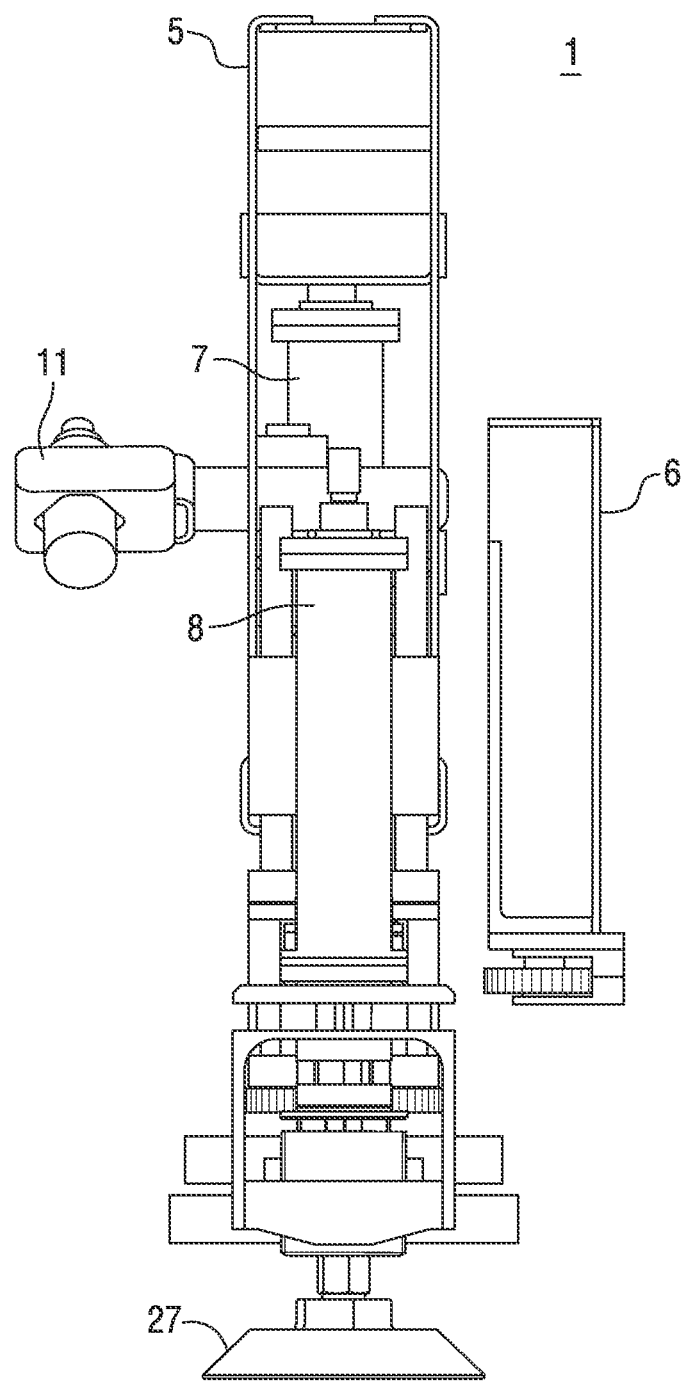
FIG. 3 is a right side view of the ultrasonic tool shown in FIG. 2, in accordance with certain embodiments of the invention.

FIG. 3 shows a right side view of the tooling 1 (as shown in FIG. 2).

Figure 4:
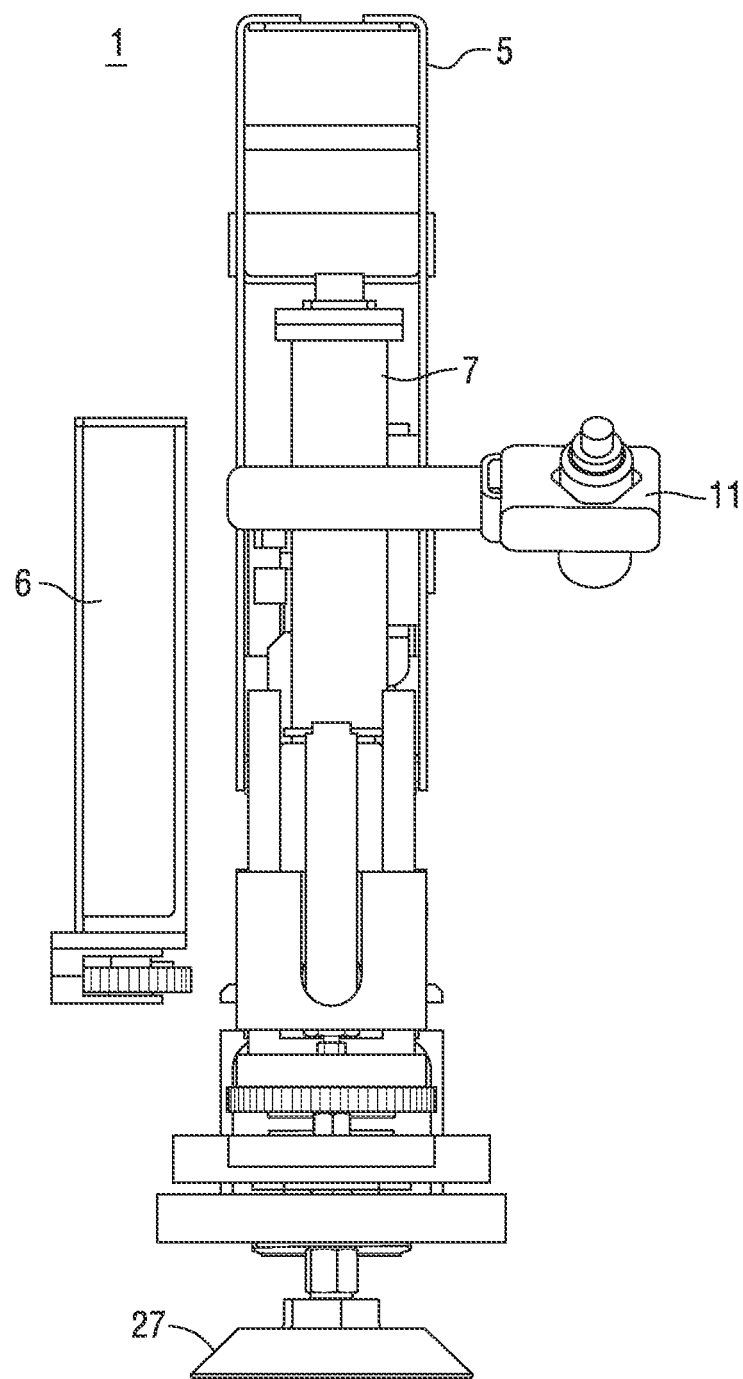
FIG. 4 is a left side view, of the ultrasonic tool shown in FIG. 2, in accordance with certain embodiments of the invention.

FIG. 4 shows a left side view of the tooling 1 (as shown in FIG. 2).

Figure 5:
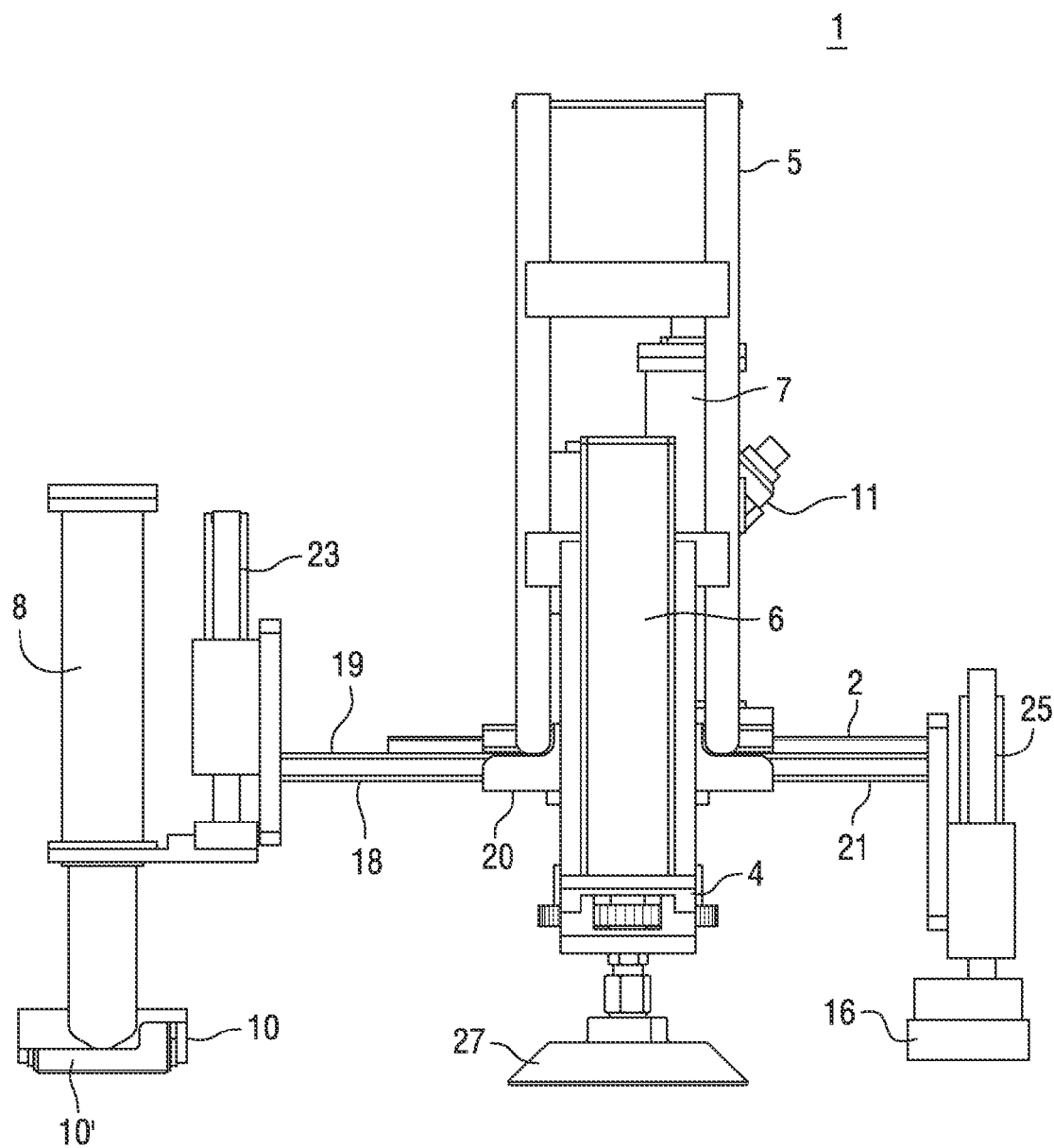
FIG. 5 is a rear view of the ultrasonic tool shown in FIG. 2, in accordance with certain embodiments of the invention.

FIG. 5 shows a back side view of the tooling 1 (as shown in FIG. 2).

Figure 6:
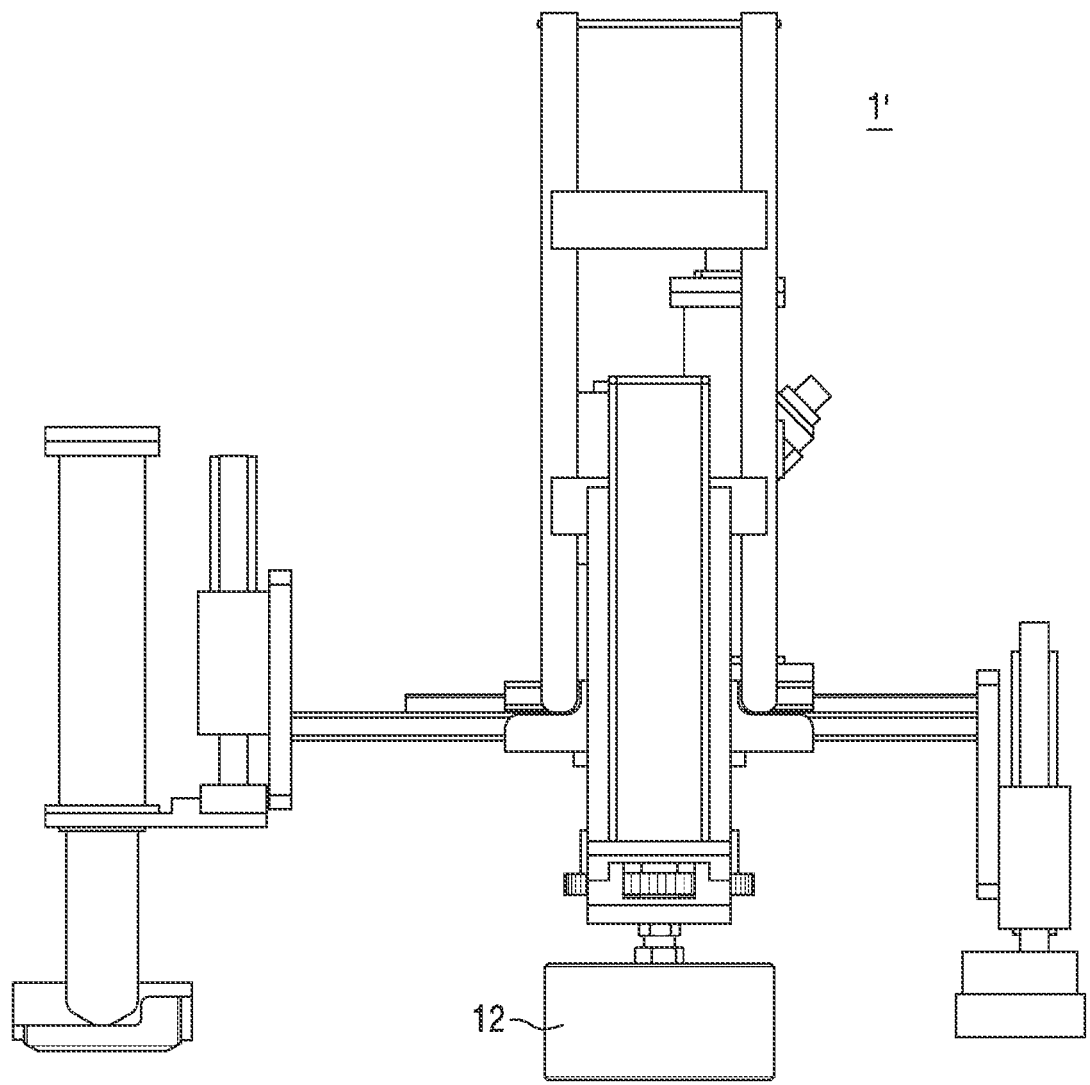
FIG. 6 is a front view of an ultrasonic tool including a base weight assembly to secure the tool in place, in accordance with certain embodiments of the invention.

FIG. 6 shows the tooling 1' in accordance with certain embodiments of the claimed invention. The tooling 1' is the same as the tooling 1 shown in FIGS. 2 through 5 with the exception that the base vacuum cup 27 in FIGS. 2 through 5 is replaced with a base weight assembly 12.

The apparatus (e.g., tool or tooling) of the invention is manually delivered to the shroud support plate using a transport mechanism such as a rope, pole or the tooling umbilical. Once located on the shroud support plate, a walking or crawling mechanism is employed to properly position the tool onto the access hole cover. In certain embodiments, the following process is employed to move the tooling on the access hole cover and to position the tooling as close as possible to (e.g., near or on) the center point of the access hole cover. The tooling is secured to the surface of the access hole cover utilizing a vacuum cup. Once secured, pneumatic linear thrusters are employed and fully raised. The tooling is then rotated by an axial rotate motor to position an arm of the tooling in a desired direction. The radial arm is fully extended in the desired direction. After being fully extended, the pneumatic linear thrusters are fully lowered to contact the surface. The vacuum cup is released and the tooling raises off the surface. The radial arm is then driven in the desired direction. After it is driven a desired distance, the pneumatic linear thrusters are raised until the vacuum cup contacts the surface. A vacuum is applied to the vacuum cup to secure the tooling to the surface and the entire process is repeated until the tooling reaches its desired location.

It is recognized that centering the tool on the access hole cover by moving the tool to a position as close as possible to the center point of the access hole cover may not be an exact process, e.g, the tool may not be positioned exactly at the center point. Thus, to account for any error in positioning the tool at the center point of the access hole cover, motion control software can be utilized. The motion control software includes an auto-centering ability that actively adjusts the three main scanning axes accordingly during scanning. This is achieved by using an ultrasonic testing data acquisition system to determine the offset distance, e.g., x and y directions or radius and angle (Cartesian or polar coordinates), from the access hole cover center point to the center of the tool. The offset is determined and the software adjusts each axis such that the scanning motion follows the same scanning profile as if the tool were exactly centered on the access hole cover. In certain embodiments due to plant configuration, planned scans with intended tooling offset (main base center to access hole cover center) may be necessary. In these embodiments, partial scans are performed. In cases where 360 degree scans are desired but not achievable from the access hole cover center, partial "pie" scans are performed with sections of each scan overlapping. These sections are then merged employing software to achieve the 360 degree scan.

In certain embodiments, the ultrasonic inspection apparatus of the invention can be modified or adapted to accommodate various designs of access hole covers such as, but not limited to, a top hat design.

While specific embodiments of the invention have been described in detail, it will be appreciated by those skilled in the art that various modifications and alternatives to those details could be developed in light of the overall teachings of the disclosure. Accordingly, the particular embodiments disclosed are meant to be illustrative only and not limiting as to the scope of the invention which is to be given the full breadth of the appended claims and any and all equivalents thereof.

What is claimed is:

1. An apparatus for ultrasonic inspection of an access hole cover weld on a core shroud support plate in a boiling water reactor containing jet pumps, the apparatus comprises:
    a base positioned on the core shroud support plate and substantially centered and secured on a surface of an access hole cover;
    a center frame coupled to the base and projecting vertically relative to the access hole cover;
    a radial arm assembly comprising a radial arm having a first end and an opposite second end, said radial arm assembly attached to the center frame;
    a radial extend/retract motor assembly coupled to the radial arm assembly and structured to control position of the radial arm radially inward and outward from the center frame;
    an axial rotate motor assembly coupled to the center frame and structured to control rotation of the center frame about a center vertical axis;
    a first pneumatic linear thruster attached to the first end of said radial arm;
    a second pneumatic linear thruster attached to the second opposite end of said radial arm, the second pneumatic linear thruster having an upper end and a lower end;
    a scanning assembly attached to the first pneumatic linear thruster, said scanning assembly, comprising:
        a skew motor assembly having an upper end and a lower end;
        a transducer gimbaling device attached to the lower end; and
        a transducer attached to the lower end of said skew motor assembly, and said transducer gimbaling device for scanning the access hole cover weld,
        wherein, said skew motor assembly is structured to control angle of the transducer relative to a normal line perpendicular to a tangential line of circumference of the access hole cover weld and the first pneumatic linear thruster is structured to extend the transducer downward for contact scanning and to retract the transducer upward for immersion scanning.

2. The apparatus of claim 1, further comprising a contact pad attached to the lower end of the second pneumatic linear thruster.

3. The apparatus of claim 1, further comprising a pneumatic cylinder connected to the first pneumatic linear thruster and positioned above the transducer to hold in place the transducer.

4. The apparatus of claim 1, wherein the base is a vacuum cup to secure attachment to a surface of the access hole cover weld.

5. The apparatus of claim 1, wherein the base is a weight assembly.

6. The apparatus of claim 1, wherein the access hole cover weld is located on a shroud support plate.

7. The apparatus of claim 1, wherein the first and second pneumatic linear thrusters are controlled independently of each other.

8. The apparatus of claim 1, further comprising an underwater camera attached to the center frame.

9. A method for ultrasonic inspection of an access hole cover weld on a core shroud support plate in a boiling water reactor having jet pumps, the method comprises:
    delivering an ultrasonic inspection apparatus to the core shroud support plate;
    positioning and securing the apparatus on the core shroud support plate and substantially centered on a surface of an access hole cover for conducting ultrasonic inspection of the access hole cover weld, the apparatus comprising:
        a base positioned on the core shroud support plate and substantially centered and secured on a surface of the access hole cover;
        a center frame coupled to the base and projecting vertically relative to the access hole cover;

a radial arm assembly comprising a radial arm having a first end and an opposite second end, said radial arm assembly attached to the center frame;

a radial extend/retract motor assembly coupled to the radial arm assembly and structured to control position of the radial arm radially inward and outward from the center frame;

an axial rotate motor assembly coupled to the center frame and structured to control rotation of the center frame about a center vertical axis;

a first pneumatic linear thruster attached to the first end of said radial arm;

a second pneumatic linear thruster attached to the second opposite end of said radial arm, the second pneumatic linear thruster having an upper end and a lower end;

a scanning assembly attached to the first pneumatic linear thruster, said scanning assembly, comprising:
- a skew motor assembly having an upper end and a lower end;
- a transducer gimbaling device attached to the lower end; and
- a transducer attached to the lower end of said skew motor assembly, and said transducer gimbaling device for scanning the access hole cover weld, employing the skew motor assembly to control angle of the transducer relative to a normal line perpendicular to a tangential line of circumference of the access hole cover weld; and employing the first pneumatic linear thruster to extend the transducer downward for contact scanning or retracting the transducer upward for immersion scanning.

10. The method of claim 9, wherein motion control software is utilized to adjust three axes during scanning.

11. The method of claim 9, wherein positioning the apparatus includes walking the apparatus along the shroud support plate to the substantial center of the access hole cover.

12. The method of claim 11, wherein walking the apparatus comprises:
- securing the base of the apparatus to the access hole cover;
- raising the first and second pneumatic linear thrusters;
- rotating the apparatus to position the radial arm in a desired direction;
- extending the radial arm to a desired distance in the desired direction;
- lowering the first and second pneumatic linear thrusters to contact the access hole cover;
- unsecuring the base of the apparatus from the access hole cover;
- raising the apparatus off of the access hole cover;
- driving the radial arm in a desired direction at a desired distance;
- raising the first and second pneumatic linear thrusters such that the base contacts the access hole cover;
- securing the apparatus to the access hole cover; and
- repeating the above steps until the apparatus is positioned in the center of the access hole cover.

* * * * *